(12) United States Patent
Eiben et al.

(10) Patent No.: US 10,373,374 B2
(45) Date of Patent: Aug. 6, 2019

(54) DEVICE, IMAGING SYSTEM AND METHOD FOR CORRECTION OF A MEDICAL BREAST IMAGE

(71) Applicant: KONINKLIJKE PHILIPS N.V., Eindhoven (NL)

(72) Inventors: Bjoern Eiben, Sutton Courtenay (GB); Sven Kabus, Hamburg (DE); Cristian Lorenz, Hamburg (DE); Thomas Buelow, Grosshansdorf (DE); David John Hawkes, Crawley (GB); John Harold Hipwell, London (GB); Vasileios Vavourakis, London (GB)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/074,469

(22) PCT Filed: Feb. 15, 2017

(86) PCT No.: PCT/EP2017/053336
§ 371 (c)(1),
(2) Date: Aug. 1, 2018

(87) PCT Pub. No.: WO2017/148702
PCT Pub. Date: Sep. 8, 2017

(65) Prior Publication Data
US 2019/0066375 A1  Feb. 28, 2019

(30) Foreign Application Priority Data

Feb. 29, 2016  (EP) .................................... 16157801

(51) Int. Cl.
*G06T 17/00* (2006.01)
*G06T 17/20* (2006.01)
(Continued)

(52) U.S. Cl.
CPC .............. *G06T 17/20* (2013.01); *A61B 5/004* (2013.01); *A61B 5/0064* (2013.01);
(Continued)

(58) Field of Classification Search
None
See application file for complete search history.

(56) References Cited

U.S. PATENT DOCUMENTS

| 8,768,022 B2 | 7/2014 | Miga et al. |
| 9,691,150 B2 | 6/2017 | Miyasa |

(Continued)

OTHER PUBLICATIONS

Han et a., "Development of patient-specific biomechanical models for predicting large breast deformation", Dec. 2011, p. 1-19 (Year: 2011).*

(Continued)

*Primary Examiner* — Robert J Craddock

(57) ABSTRACT

The present invention relates to device and method for correction of a medical breast image. To provide for an improved correction, said device comprises a medical image input (31) for obtaining a medical breast image of subject's breast potentially showing artificial deformations of the breast, a scan image input (32) for obtaining a scan image of the same subject's breast showing the breast in a predetermined position of the subject and comprising surface information of the breast, a simulation unit (33) for generating a simulated medical breast image from the obtained medical breast image, said simulated medical breast image showing the breast in the same predetermined position of the subject as the scan image and representing the breast surface by a surface mesh, wherein said simulation unit (33) is configured to generate said simulated medical breast image based on a volumetric biomechanical model, and wherein material parameters of the biomechanical model are varied for aligning the biomechanical model with the breast surface (Continued)

extracted from the scan image, and a correction unit (34) for determining corrections for correcting the simulated medical breast image for said artificial deformations by use of the scan image by applying a surface matching between said surface mesh and said scan image and for applying the determined corrections to the obtained medical breast image to obtain a corrected medical breast image.

20 Claims, 3 Drawing Sheets

(51) Int. Cl.

| | |
|---|---|
| A61B 6/03 | (2006.01) |
| A61B 5/055 | (2006.01) |
| A61B 5/00 | (2006.01) |
| G06T 7/30 | (2017.01) |
| A61B 6/00 | (2006.01) |
| G06T 3/00 | (2006.01) |
| G06T 5/00 | (2006.01) |
| G06T 15/08 | (2011.01) |
| G01R 33/56 | (2006.01) |

(52) U.S. Cl.
CPC ............ *A61B 5/0091* (2013.01); *A61B 5/055* (2013.01); *A61B 5/4312* (2013.01); *A61B 6/032* (2013.01); *A61B 6/502* (2013.01); *A61B 6/5217* (2013.01); *G06T 3/0093* (2013.01); *G06T 5/002* (2013.01); *G06T 7/30* (2017.01); *G06T 15/08* (2013.01); *G06T 17/00* (2013.01); *A61B 6/5247* (2013.01); *G01R 33/5608* (2013.01); *G06T 2200/04* (2013.01); *G06T 2207/10072* (2013.01); *G06T 2207/10081* (2013.01); *G06T 2207/10088* (2013.01); *G06T 2207/20182* (2013.01); *G06T 2207/20221* (2013.01); *G06T 2207/30068* (2013.01)

(56) References Cited

U.S. PATENT DOCUMENTS

| | | |
|---|---|---|
| 2014/0044333 A1 | 2/2014 | Barth et al. |
| 2014/0288420 A1 | 9/2014 | Goossen et al. |
| 2015/0126864 A1 | 5/2015 | Buclow et al. |

OTHER PUBLICATIONS

Schnabel et al., "Validation of Nonrigid Image Registration Using Finite-Element Methods: Application to Breast MR Images", Feb. 2003, p. 238-247 (Year: 2003).*

Eiben, B. et al., "Biomechanically guided prone-to-supine image registration of breast MRI using an estimated reference state." Biomedical Imaging (ISBI), 2013 IEEE 10th International Symposium, pp. 214-217 (2013).

Nelder, J. et al., "A simplex method for function minimization,". The Computer Journal 7(4), 308-313 (1965).

Field, D.A., "Laplacian smoothing and delaunay triangulations," Communications in Applied Numerical Methods 4(6), 709-712 (1988).

Lago, M.A. et al., "Breast prone-to-supine deformation and registration using a Time-of-Flight camera", Biomedical Robotics and Biomechatronics, 2012 4th IEEE Ras&EMBS International Conference on, IEEE 24 Jun. 10, 2012, pp. 1161-1163.

Rajagopal, V. et al., "Modeling breast biomechanics for multi-modal image analysis—successes and challenges", Wiley Interdisciplinary Reviews: Systems Biology and Medicine, vol. 2, No. 3, May 1, 2010, Abstract.

Carter, T. et al., "MR Navigated Breast Surgery: Method and Initial Clinical Experience", D. Metaxas et al. (Eds.): MICCAI 2008, Part II, LNCS 5242, pp. 356-363, 2008.

Yeh, E.D., et al., "Positioning in Breast MR Imaging to Optimize Image Quality", RadioGraphics 34(1), El (E17) (2014).

Veronda, D.R. et al., "Mechanical characterization of skin-Finite deformations". Journal of Biomechanics, 19700101 Pergamon Press, New York, vol. 3, Nr: 1, p. 111-122, IN9, 123-124.

* cited by examiner

DEVICE, IMAGING SYSTEM AND METHOD FOR CORRECTION OF A MEDICAL BREAST IMAGE

CROSS-REFERENCE TO PRIOR APPLICATIONS

This application is the U.S. National Phase application under 35 U.S.C. § 371 of International Application No. PCT/EP2017/053336, filed on Feb. 15, 2017, which claims the benefit of European Patent Application No. 16157801.8, filed on Feb. 29, 2016. These applications are hereby incorporated by reference herein.

FIELD OF THE INVENTION

The present invention relates to a device and method for correction of a medical breast image as well as to an imaging system.

BACKGROUND OF THE INVENTION

A difficulty in breast imaging, breast surgery and treatment planning is the fact that the shape of the breast changes significantly with the positioning of the patient, e.g., prone position during acquisition of an MRI image and supine position during surgery or radiotherapy and upright position during optical surface imaging. Alignment of the different views of the breast can be employed to solve this issue in surgical planning and guidance or radiotherapy planning.

To align the different views, standard image based registration is usually not possible since in the standard clinical workflow supine (or even upright) volumetric images are not acquired. Acquisition of these additional images would add a significant complication (time, cost, and inconvenience for the patient) to the workflow and is unlikely to become common practice.

Prone-to-supine breast image registration by inclusion of a biomechanical model, as described in Eiben, B., Han, L., Hipwell, J., Mertzanidou, T., Kabus, S., Buelow, T., Lorenz, C., Newstead, G., Abe, H., Keshtgar, M., Ourselin, S., Hawkes, D.: Biomechanically guided prone-to-supine image registration of breast MRI using an estimated reference state. In: Biomedical Imaging (ISBI), 2013 IEEE 10th International Symposium on. pp. 214-217 (2013), has been found to be promising and successful in many cases. However, between the upright simulation and the optically scanned breast surface (also in upright position) a sufficiently good alignment is not guaranteed. This is to some extent due to the MRI scanning and patient support equipment. Even breasts of carefully positioned patients can show severe skin surface indentations (e.g., due to the MRI coils) especially in the medial region around the sternum.

US 2014/0044333 A1 discloses a system and method for providing registration between breast shapes before and during surgery. A registration framework is presented that registers volumetric breast images captured before surgery with intraoperative surface images. The method comprises the steps of: identifying an air/tissue boundary from a volumetric image created at a first time; processing the volumetric image with an image filter to emphasize the air/tissue boundary; and registering a surface optically scanned image with the filtered volumetric image, where the surface optically scanned image is created at a second time.

SUMMARY OF THE INVENTION

It is an object of the present invention to provide a device, system and method for improved correction of a medical breast image, in particular for deformations caused by equipment used for acquisition of the medical breast image.

In a first aspect of the present invention a device for correction of a medical breast image is presented said device comprising:
  a medical image input for obtaining a medical breast image of subject's breast potentially showing artificial deformations of the breast,
  a scan image input for obtaining a scan image of the same subject's breast showing the breast in a predetermined position of the subject and comprising surface information of the breast, wherein said simulation unit is configured to generate said simulated medical breast image based on a volumetric biomechanical model, and wherein material parameters of the biomechanical model are varied for aligning the biomechanical model with the breast surface extracted from the scan image,
  a simulation unit for generating a simulated medical breast image from the obtained medical breast image, said simulated medical breast image showing the breast in the same predetermined position of the subject as the scan image and representing the breast surface by a surface mesh, and
  a correction unit for determining corrections for correcting the simulated medical breast image for said artificial deformations by use of the scan image by applying a surface matching between said surface mesh and said scan image and for applying the determined corrections to the obtained medical breast image to obtain a corrected medical breast image.

In a further aspect of the present invention an imaging system is presented comprising:
  an medical image acquisition unit for acquiring a medical breast image of subject's breast potentially showing artificial deformations of the breast,
  a scan image acquisition unit for acquiring a scan image of the same subject's breast showing the breast in a predetermined position of the subject and comprising surface information of the breast,
  a device as disclosed herein for correction of a medical breast image acquired by said medical image acquisition unit by use of the acquired scan image, and
  an output unit for outputting the corrected medical breast image.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed system, in particular as defined in the dependent claims and as disclosed herein.

The present invention is based on the idea to correct medical breast images (e.g. breast MRI images or mammographic images) for deformation, e.g. skin surface indentations (caused e.g. by the coil design of breast coils used in breast MRI imaging). These deformations, e.g. indentations, are visible in medical breast image, e.g. in a prone MRI image, and propagate to simulated breast shapes in other patient positions such as upright or supine position. Correction is done based on a simulated breast shape (i.e. a simulated medical breast image in a particular position, e.g. the upright position) generated from the original medical breast image (e.g. a prone MRI scan) and a scan image comprising (3D) surface information of the breast (e.g. a 3D optical surface scan). In other words, the scan image must be such that it is possible to extract surface information. For this correction a surface matching is applied between the simulated medical breast image and the scan image.

It shall be noted that it may not be known beforehand whether the medical breast image actually shows artificial deformations of the breast or not. Hence, reference is made to a medical breast image potentially showing artificial deformations. Alternatively, reference can simply be made to a medical breast image of a subject's breast. Despite that uncertainty, the medical breast image is treated as if it contained such deformations. Artificial deformations can refer to non-natural deformations, e.g. induced by effects other than gravity such as deformations caused by equipment used for acquisition of the medical breast image.

For instance, the residual error between an upright simulation (e.g. derived from a prone MRI) and an optical surface scan may be corrected by imposing a displacement constraint on the skin nodes such that these nodes coincide with the skin surface acquired with a 3D optical scanner. Hence, said correction unit may be configured to determine said corrections by imposing a displacement constraint on skin nodes of said surface mesh such that said skin nodes coincide with the skin surface represented by the surface scan image. One possible implementation of this correction step makes use of a surface matching step. Another challenge related to the clinical applicability of a patient specific biomechanical model is, that the material parameters are often not known and wide stiffness variations were reported in the literature. It is thus proposed to vary material parameters of the biomechanical model such that (surface of) the biomechanical model aligns with the breast (target) surface extracted from the scan image.

In an embodiment said simulation unit is configured to rigidly align the generated surface mesh to the breast surface extracted from the scan image to optimize the material parameters of the biomechanical model. The volumetric biomechanical model can thus be updated based thereon, i.e., based on the result of said optimization.

In an embodiment the simulation unit (33) is configured to vary material parameters of the biomechanical model comprising a shear modulus and/or a bulk modulus.

In an embodiment said correction unit is configured to determine a displacement vector field indicating the local corrections of said surface mesh and to apply said displacement vector field to the obtained medical breast image to obtain the corrected medical breast image. Such a displacement vector field comprises a plurality of displacement vectors for a plurality of locations and allows a rather precise correction.

The simulation unit may be configured to generate a simulated medical breast image, in which the breast is represented by a volumetric mesh including said surface mesh and a volume mesh. Such a volumetric mesh (also called FE (Finite Elements) mesh, is a mathematical representation of a biomechanical model used for numerical simulations and may include tetrahedral volume elements (forming the volume mesh) representing the breast tissue and triangular membrane elements (forming the surface mesh) representing the skin. A biomechanical model is a geometric representation of the organ (e.g. in form of a tetrahedral mesh) equipped with locally resolved mechanically relevant information such as density and elasticity.

By use of the volumetric mesh a surface warping is advantageously applied by the correction unit. Such a surface warping may comprise one or more steps for performing the correction with increased accuracy and efficiency.

In one embodiment said correction unit is configured to determine said corrections by applying a displacement calculation for driving the surface mesh towards the surface scan image, i.e. for driving the skin surface of the biomechanical model towards a target mesh that is used as target in the mesh warping step, which is the surface mesh of the scan image. This provides a desired alignment of the two meshes.

In another embodiment said correction unit is configured to determine said corrections by applying a smoothing, in particular a Laplacian mesh smoothing, for regularizing the volume mesh. This steps acts as a smoothing of the correction step. For instance, a linear correction is preferred over an oscillating (whereby linear and oscillating refer to a profile taken out of the correction surface); in other words, a homogeneous correction surface is preferred over an inhomogeneous correction surface.

In another embodiment said correction unit is configured to apply an area constraint for reducing local changes in the surface area of the breast surface. This maintains the area of each mesh sub-area (e.g. triangle) of the mesh surface. From a computational and from a modeling point of view a mesh with more or less equal triangle area sizes is preferred over one with very few and very small sub-areas (e.g. triangles).

In another embodiment said correction unit is configured to apply a self-intersection prevention for avoiding mesh intersections. This provides to obtain a well-defined mesh surface with no mesh intersections.

Generally, any medical breast image may be corrected by use of the present invention. Preferably, said medical breast image is a CT image, in particular a supine CT image, an MRI image, in particular a prone MRI image, or a mammographic image. The scan image can generally be any scan image showing the breast in any position. Preferably, said scan image is an upright scan image, wherein said simulation unit is configured to generate an upright simulated medical breast image.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
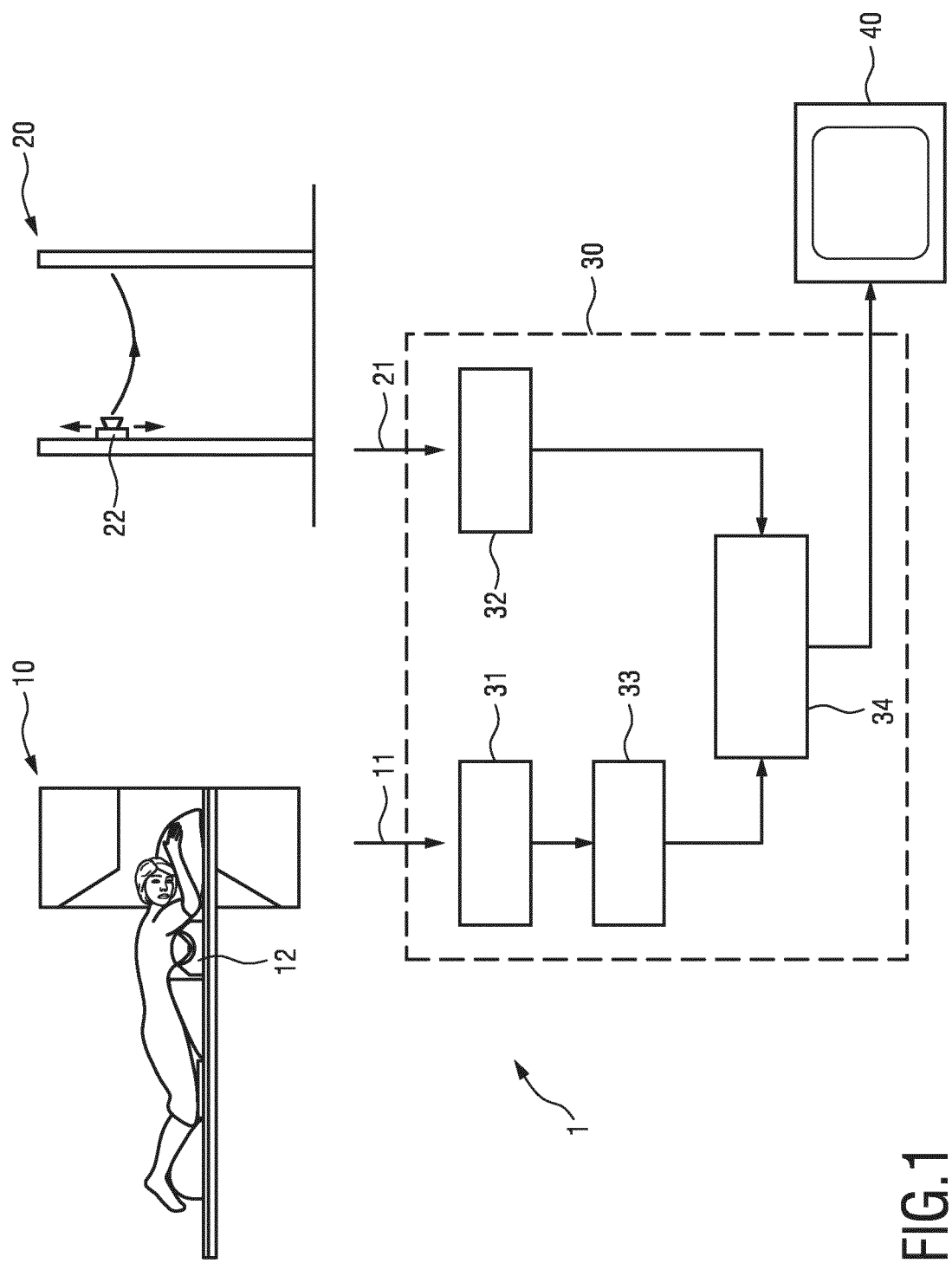
FIG. 1 shows a schematic diagram of an embodiment of an imaging system and a device according to the present invention.

FIG. 1 shows a schematic diagram of an embodiment of an imaging system 1 and a device 30 for correction of a medical breast image according to the present invention.

The imaging system 1 comprises a medical image acquisition unit 10 for acquiring a medical breast image of subject's breast potentially showing artificial deformations of the breast. In this exemplary embodiment the medical image acquisition unit 10 is an MRI (magnetic resonance image) acquisition unit for acquiring a prone breast MRI image 11 by use of a breast coil 12 and further elements of a conventional MRI acquisition unit. The breast coil 12 is arranged around the breast and often causes indentations, which are visible in the MR image and shall be corrected by the device 30.

The imaging system 1 further comprises a scan image acquisition unit 20 for acquiring a scan image 21 of the same subject's breast showing the breast in a predetermined position of the subject. In this exemplary embodiment the scan image acquisition unit 20 is a 3D optical scanner, in which an optical camera 22 rotates around the subject to acquired image data forming a scan image of the subject, at least of the subject's breast.

The imaging system 1 further comprises a device 30 for correction of a medical breast image 11 acquired by said medical image acquisition unit 10 by use of the acquired scan image 21. The device 30 may e.g. be a processor, computer, workstation, and may be implemented in software and/or hardware.

The imaging system 1 further comprises an output unit 40 for outputting the corrected medical breast image. The output unit 40 may e.g. be a display for displaying the corrected medical breast image for diagnostic purposes by a physician.

Breast cancer is the most common cancer for women worldwide and in the UK women bear a lifetime risk of one-in-eight to develop this disease. Detection, diagnosis and interventions could benefit from combining information of different images or aligning images and the contained information with a surgical or interventional setting. To achieve this goal, establishing accurate correspondence between images or between images and a real world setting is required. The breast is a soft organ and is subject to large deformations when the patient position is changed. Different procedures require different patient setups to optimize image acquisition (e.g. prone MRI), improve patient stability and comfort (e.g. supine radiotherapy treatment), or account for practical circumstances (e.g. supine surgical position).

Prone-to-supine breast image registration aims to establish correspondence between images in the presence of large deformations. Standard intensity based image registration alone is unlikely to produce sufficient alignment due to the lack of initial overlap between the images. But since gravity is the main source of breast deformation between patient positions, continuum mechanics based knowledge can be exploited to predict gravity induced deformations. Such deformations can in turn be effectively used to guide registration procedures. While some known approaches use mechanical simulations alone to predict one patient configuration from the other, alternative strategies combine biomechanical simulations with standard image registration methods or aim for a higher level of integration between simulation and registration.

Pre-surgical prone Dynamic Contrast Enhanced (DCE) MR images are part of the standard clinical procedure for some patients and provide important information about the extent and location of the cancerous tissue. This motivates the use of DCE MR images to guide surgical procedures. In the current clinical workflow however, 3D prone-supine image pairs are usually not available at the time of surgery, which potentially limits the use of image driven registration approaches. Supine CT images for instance are only acquired after surgery to facilitate planning of dose delivery for radiotherapy. Another challenge related to the clinical applicability of a patient specific biomechanical model is, that the material parameters are often not known and wide stiffness variations were reported in the literature. This motivated material parameter optimization.

In the context of image guided breast surgery, supine breast MRI might provide information about the extent and location of a lesion in the surgical position. Hence this configuration was utilized in studies to assess the feasibility of image guided breast interventions. However, to date the supine imaging position is not standard clinical practice. Optical surface imaging techniques have become popular in recent years. This fast, non-invasive and, compared to MRI, relatively low cost imaging modality could be used to image the patient in an upright or supine surgical pose. This could provide a valuable adjunct to prone pre-operative MRI, for surgical planning, surgical guidance or cosmetic evaluation when the prone image is warped towards a target surface.

According to an aspect of the present invention an image-to-surface registration method is proposed, which, in embodiments, incorporates finite element (FE) biomechanical modeling, material parameter optimization and surface warping to transform prone MR images to a supine or upright target surface. For validation purposes the target surface may be extracted from a supine radiotherapy planning CT scan, to allow evaluation of the target registration error (TRE) within the breast volume. Details of an exemplary non-limiting scenario are explained in the following.

Prone MRI and supine CT images (used for validation only, but not needed or available in a practical scenario) are segmented by first delineating the patient's skin surface. MR images are further processed and the surface of the pectoralis muscle is identified to define the posterior boundary of the biomechanical model. Internal breast structures are then further segmented into adipose and fibro-glandular tissues using e.g. an expectation maximization based image segmentation. With the segmentation in place, the breast geometry is discretized into an FE mesh consisting of tetrahedral volume elements to represent the breast tissue and triangular membrane elements to represent the skin. Each element is labeled according to the tissue class segmentation result. The constitutive relation for the fat and fibroglandular tissue was selected to be $$\overline{W}_{tissue} = \frac{\mu}{2}(\tilde{I}_1 - 3) + \frac{\kappa}{2}(J - 1)^2, \quad (1)$$

where $\mu$ and $\kappa$ are the material parameters in terms of the shear and bulk modulus respectively, J is the determinant of the deformation gradient, and $\tilde{I}_1$ is the first invariant of the deviatoric right Cauchy-Green tensor. For the skin membrane elements the exponential constitutive relation $$\overline{W}_{skin} = \alpha_s(e^{\beta_S s^{(\tilde{I}_1-3)}}-1)+c_s(\tilde{I}_2-3) \quad (2)$$

according to Veronda and Westmann (as disclosed in Veronda, D. R. and Westmann, R. A., "Mechanical characterization of skin—finite deformations," Journal of Biomechanics 3(1), 111-124 (1970)) is used, where $\tilde{I}_1$ and $\tilde{I}_2$ denote the first and second invariant of the two-dimensional Cauchy-Green strain tensor and $\alpha_S$, $\beta_S$ and $c_S$ are material parameters.

The boundary conditions of the breast model are selected such that the breast-chest interface is regarded as fixed, whereas the skin is assumed to be traction free. Nodes on the superior and inferior planes are restricted to axial in-plane motion.

Figure 2:
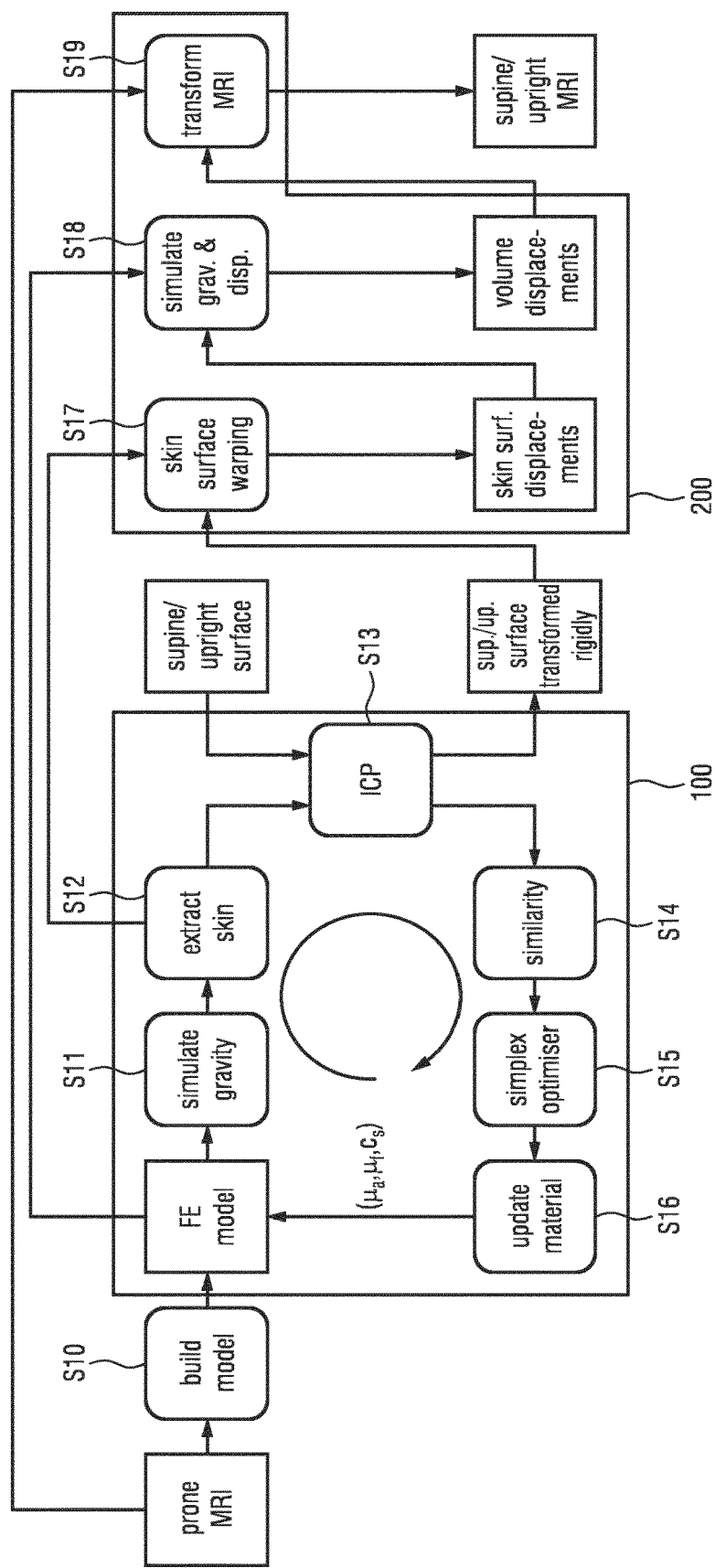
FIG. 2 shows a schematic diagram of an exemplary workflow for use with the present invention.
Figure 3A:
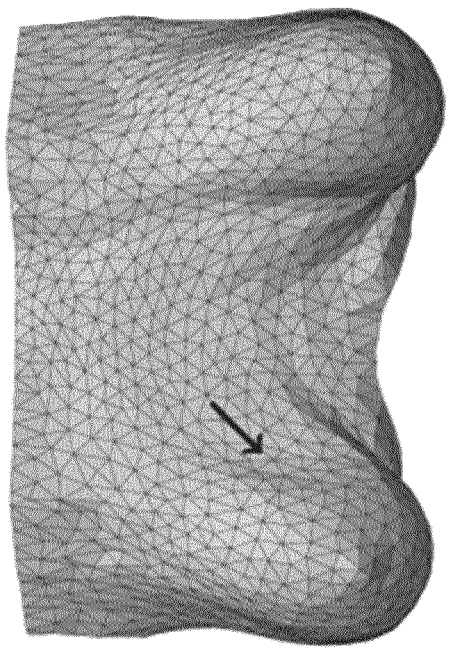
FIG. 3 shows various images illustrating various elements of the present invention.
Figure 3B:
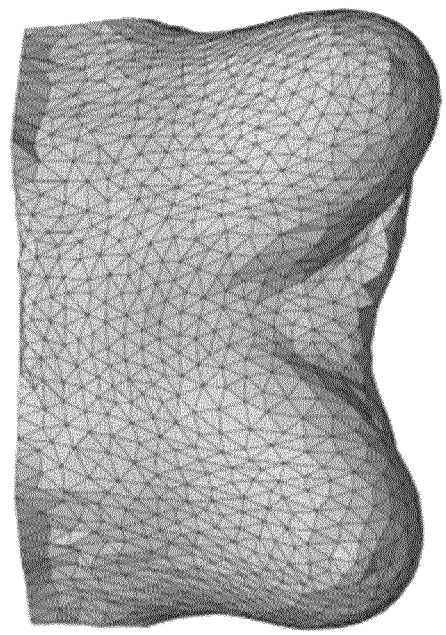
Figure 3C:
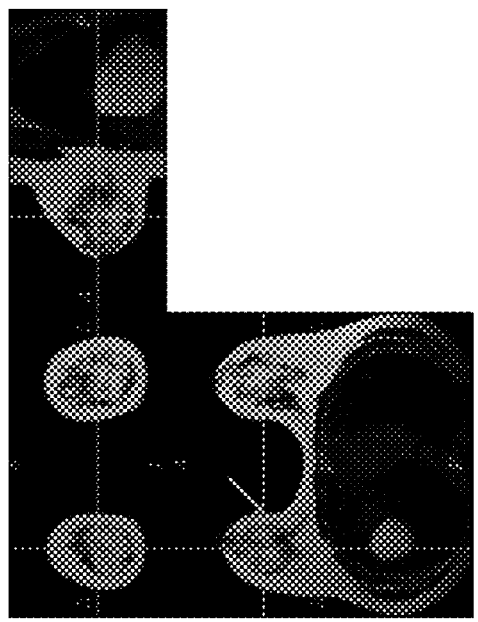
Figure 3D:
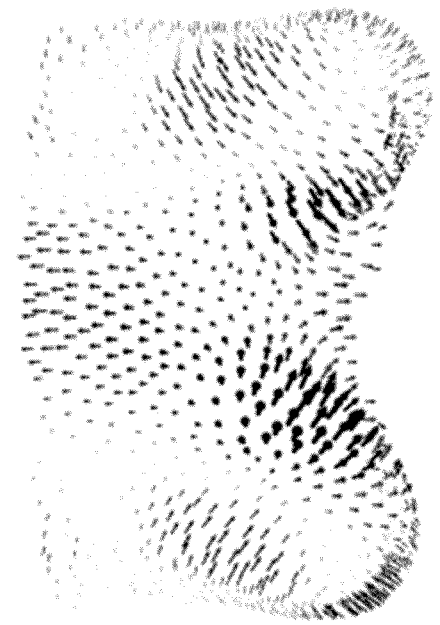

FIG. 2 shows an overview of the material optimization strategy which in an embodiment may form the first step of the proposed correction method. The prone MRI based biomechanical model is generated in step S10 as described below and together with the target image forms the input of the optimization.

The purpose of the optimization procedure is to align the biomechanical model and the target surface as well as possible by only varying the material parameters of the biomechanical model. To this end the shear modulus μ is optimized for fat and fibroglandular tissue while using a fixed ratio between these tissue class stiffness values. The bulk modulus λ on the other hand is set so that it resembles a constant Poisson's ratio accounting for a near incompressible behavior of the simulated tissues. For the skin $c_s$ is selected as the free parameter in the optimization procedure since it is associated with $\tilde{I}_2$ which in turn can be interpreted as a measure for surface area change.

The biomechanical simulation in step S11 comprises two steps. In the first step the effects of gravity are removed by estimating an unloaded configuration. In the second step gravity is simulated corresponding to the configuration of the target surface (i.e. supine or upright). In the simulated target configuration the skin surface is extracted from the model in step S12 in order to facilitate rigid alignment with the target surface using an iterative closest point algorithm (ICP) in step S13. Since changes of the material parameters also affect the rigid alignment between the simulation and the target surface, the ICP is run repeatedly after each simulation.

The registration quality between the loading simulation and the target surface is evaluated with an objective function in step S14. For this purpose the mean Euclidean point-to-surface distance is used. Let $P_{sim}(\mu_f, \mu_g, c_s) = \{P_1, P_2, \ldots, P_N\}$ be the N points of the moving surface mesh, i.e. the extracted skin points of the biomechanical loading simulation. Furthermore let $S_{scan}$ be the target surface, then the objective function is given by the mean minimum distance d of each point to the surface $$m = \frac{1}{N} \sum_{i=1}^{N} d(P_i, S_{scan}). \tag{3}$$

FIG. 2 shows an overview of an exemplary embodiment of a method according to the present invention reflecting a possible workflow. The method comprises a material parameter optimization workflow 100 and a subsequent warping workflow 200.

The outputs of the material parameter optimization workflow 100 are the material parameters, as well as the homogeneous rigid matrix which is used to produce a transformed surface mesh $S'_{rigid}$. As can be seen from FIG. 2, the evaluation of the objective function in step S14 involves a series of computations, including two biomechanical simulations, and application of an iterative closest point algorithm. These steps in particular make the process computationally expensive. Furthermore a gradient of the objective function is not available. Hence Nelder-Mead simplex algorithm (as disclosed in Nelder, J. A. and Mead, R., "A simplex method for function minimization," The Computer Journal 7(4), 308-313 (1965)) is used as an optimizer in step S15 that determines the updated material parameters in step S16.

Optimized material parameters alone do not necessarily guarantee a sufficiently good alignment between the loading simulation and the corresponding scanned surface. This is to some extent due to the MRI scanning and patient support equipment. Even breasts of carefully positioned patients can show severe skin surface indentations especially in the medial region around the sternum, e.g. due to the used breast coils 12 (see FIG. 1). One way to approach this deformation in a biomechanical simulation would be additional surface forces, which counteract this deformation. However, the local varying magnitude of such forces is not known and thus cannot be introduced in the simulation. A simpler alternative is required and is proposed herein.

According to an embodiment of the present invention the residual alignment error of the loading simulation is corrected by imposing a displacement constraint on the skin nodes such that these nodes coincide with the skin target surface. A simple closest distance projection onto the 3D target skin surface may be insufficient since (i) the projection could result in significant surface area changes and in extreme cases in collapsing elements (ii) the resulting surface elements could be of bad quality and (iii) the displacements are not necessarily smooth.

An exemplary embodiment of the surface warping workflow 200 is shown in block 200 of FIG. 2. The material parameter optimization 100 aligns the finite element biomechanical model with the supine (or upright) surface scan. The material parameters of the biomechanical model are optimized so that the rigid alignment of the surface scan and the simulated corresponding position improves the similarity measure. To obtain the final surface driven alignment, the extracted skin surface from the biomechanical model is non-rigidly warped in step S17 to fit the rigidly transformed supine or upright target mesh. This warping step results in skin-surface displacements that are subsequently used in step S18 to update the volumetric biomechanical model: Gravity is first simulated as in the material parameter optimization step S11, then the surface displacements are applied to the skin nodes. This biomechanical gravity/displacement simulation generates volumetric displacements across the whole region of interest and allows the original MR image to be transformed accordingly in the final step S18.

More details of the various optional components of the proposed surface warping technique are described in the following and comprise a displacement calculation D, which drives the skin surface of the biomechanical model towards the target mesh, a Laplacian mesh smoothing step, L, which regularizes the mesh, an area constraint, A, which reduces local changes in surface area and finally a self-intersection prevention, I, which avoids mesh intersections.

For the displacement calculation let K be the nodal connectivity matrix of the skin surface mesh. A matrix with smoothing characteristics can be computed by calculating its $m_D$-th power. Furthermore let the vector with the closest distances pointing from the current nodal positions $P_i^{A,n}$ at iteration n to the surface $S'_{scan}$ be $$d = \{d_1(P_1^{A,n}, S'_{scan}), d_2(P_2^{A,n}, S'_{scan}), \ldots\},$$

then a smooth version of the displacements can be calculated according to $d' = K^{m_D} d$. These smoothly varying displacements are used to update the nodal positions according to the following iterative scheme:

$$P_i^{D,n} = P_i^{A,n-1} + sd'_i. \tag{4}$$

Here s is a scaling parameter which is used to balance the displacement driven component of the deformation with the other constraints.

Mesh regularity often is a desired quality in biomechanical simulations. To control this during the course of the iterations, Laplacian Mesh Smoothing is used (as e.g.

described in Field, D. A., "Laplacian smoothing and delaunay triangulations," Communications in Applied Numerical Methods 4(6), 709-712 (1988)). This is particularly useful in cases where the simulated surface normal shows a large angle to the target surface. In such extreme cases the displacement step D could cause the moving elements to collapse. Hence let $w(P_i^{D,n})$ be the set of indices of mesh points connected to point $P_i^{D,n}$ and be $|w|$ the number of neighbors, then the displaced node $P_i^L$ can be computed as $$P_i^{L,n} = (1-l)P_i^{D,n} + \frac{l}{|w|}\sum_{j \in w} P_j^{D,n}. \quad (5)$$

This means, that each point aims to move towards the centre of the surrounding points. The scalar weight l which in all processed cases was selected to be l=0.1 controls the amount of smoothing.

Both previous mesh warping steps can introduce local changes to the surface area. In order to reduce the area change, a correction vector is calculated for each node as follows. Let $T=\{T_1, \ldots, T_j\}$ be the triangular surface elements connected to the current node $P_i^{L,n}$. For each element a deviation from the original surface area $A_0, T_m$ (i.e. the area of each triangle before the surface warping is initiated) can be calculated $$a_{T_m} = \frac{\|v_{T_m} \times w_{T_m}\|}{2A_{0,T_m}} - 1. \quad (6)$$

Here the vectors $vT_m$ and $wT_m$ point from the current central node to the opposite nodes of the triangle $T_m$. The final correction vector is calculated as $$P_i^{A,n} = P_i^{L,n} + \sum_{t \in T} a_t \frac{v_t \times w_t}{\|v_t \times w_t\|}. \quad (7)$$

Updating the node positions can result in a self-intersecting mesh. This is most likely the case in the inframammary fold region when the upright position is used as a target configuration. Hence, an intersection prevention process may be incorporated by sensing possible surface contact in the direction of motion. If a self-intersection is detected, the corresponding node is kept fixed.

FIG. 3 shows the impact of contact between the breast and the MR scanner (i.e. the breast coil) in the prone configuration and an example result of the surface warping methodology as described above. FIG. 3A shows the prone MRI (i.e. an acquired medical breast image), wherein the arrow indicates contact of the breast with the scanner. FIG. 3B shows the simulated upright surface (i.e. the simulated medical breast image) after the material optimization step. The contact of the MRI breast coil propagates to the simulation result, as indicated by the arrow. To correct for this effect, a displacement vector field is calculated as shown in FIG. 3C by use of the surface warping. Application of the displacements to the simulated surface results in a corrected surface (i.e. a corrected medical breast image) as shown in FIG. 3D.

As can be seen in FIG. 3, the deformations that originate from contact of the patients' breast with the MRI coil are effectively reduced. The displacement vector field shows the largest amplitude in the medial breast region. Hence, the corrected mesh represents the actual upright surface more precisely.

In a final step the surface displacements calculated as explained above may be used to update the volume mesh of the biomechanical model with the optimized material parameters obtained earlier. Hereby, gravity loading and nodal displacement conditions are considered simultaneously. To calculate the volumetric displacements, the last loading simulation from the material parameter optimization may be re-initiated. When the gravity loading is completed, the displacement boundary condition on the skin surface nodes is activated. This imposes the previously calculated surface displacements onto the biomechanical simulation.

The volumetric displacements are now completely defined and can be generated by composing the deformation vector fields of (i) the unloading, (ii) the reloading, and (iii) the prescribed displacement simulations. This allows image warping and landmark transformation from the prone into the loaded configuration to be performed.

In summary, surface driven prone-to-supine registration with a future application in image guided surgery faces the challenge that the target information likely is not a three-dimensionally resolved image, but potentially an optical surface scan. Hence algorithms are required, which enable the deformation of prone MR images into the supine position using target surface information. According to the present invention a registration scheme (or image correction method) is proposed which overcomes two main challenges when biomechanical models are used to simulate the large deformation, in particular from prone to supine or upright, namely (i) the unknown material parameters as well as (ii) additional deformations introduced by the MRI scanning equipment in the prone position. This is achieved by a material optimization procedure followed by surface warping step which corrects residual geometric differences between the biomechanical simulation and the target surface.

Considering that no internal information was used to drive the registration, this method has great potential to aid navigation in a surgical setting. The benefits of the surface driven approach are twofold. Regarding the clinical application the prone-supine registration can be utilized for surgical planning and initial guidance, since the lesion extent and margin visualization becomes possible in multiple poses, namely supine, prone and upright. From the biomechanical modeling perspective the information obtained from the material optimization and surface warping could be utilized in a feedback step to improve the biomechanical model geometry by removing the MRI coil deformation artifacts which then leads to an updated estimation of the unloaded configuration.

It shall be noted that the above explanation related to the figures is an exemplary embodiment. The invention can also be applied to other medical breast images acquired with other image acquisition equipment, such as mammographic images, CT images or ultrasound images (which may show deformation artifacts caused by the ultrasound device), and/or acquired in other positions of the subject, such as supine image or upright images. The scan image can be acquired with any scan image acquisition equipment, such as an optical camera, a body scanner, a hand-held scanning device, etc. Both images can be acquired one after the other and can be directly processed right after acquisition, but it is also possible that one or both images are acquired in advance and stored and processed at a later time. If the medical breast image and the scan image are acquired with the subject being in the same position (e.g. the upright position or the prone position) the step of determining the simulated breast image to bring it into the same position as the scan image may be omitted.

In a further embodiment, a device for correction of a medical breast image is presented said device comprising: a medical image input for obtaining a medical breast image of subject's breast potentially showing artificial deformations of the breast; a scan image input for obtaining a scan image of the same subject's breast showing the breast in a predetermined position of the subject; a simulation unit for generating a simulated medical breast image from the obtained medical breast image, said simulated medical breast image showing the breast in the same predetermined position of the subject as the scan image and representing the breast surface by a surface mesh; and a correction unit for determining corrections for correcting the simulated medical breast image for said artificial deformations by use of the scan image by applying a surface matching between said surface mesh and said scan image and for applying the determined corrections to the obtained medical breast image to obtain a corrected medical breast image. Further, there are provided a corresponding method, a computer program, a non-transitory computer-readable recording medium and an imaging system comprising said device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device comprising:
   a medical image input circuit that receives a medical breast image of a subject's breast potentially showing artificial deformations of the breast,
   a scan image input circuit that receives a scan image of the subject's breast showing the breast in a predetermined position of the subject and comprising surface information of the breast surface,
   a simulation circuit that generates a simulated medical breast image from the obtained medical breast image, the simulated medical breast image showing the breast in the same predetermined position of the subject as the scan image and representing the breast surface by a surface mesh,
   wherein the simulation circuit is configured to generate the simulated medical breast image based on a volumetric biomechanical model, and
   wherein material parameters of the biomechanical model are varied for aligning the biomechanical model with the breast surface extracted from the scan image, and
   a correction circuit that determines corrections to correct the simulated medical breast image for the artificial deformations based on the scan image by applying a surface matching between the surface mesh and the scan image, and applies the determined corrections to the obtained medical breast image to provide a corrected medical breast image.

2. The device of claim 1, wherein the simulation circuit is configured to rigidly align the generated surface mesh to the breast surface extracted from the scan image to optimize the material parameters of the biomechanical model.

3. The device of claim 1, wherein the correction circuit is configured to determine a displacement vector field indicating local corrections of the surface mesh and to apply the displacement vector field to the obtained medical breast image to obtain the corrected medical breast image.

4. The device of claim 1, wherein the correction circuit is configured to determine the corrections by imposing a displacement constraint on skin nodes of the surface mesh such that the skin nodes coincide with the skin surface represented by the surface scan image.

5. The device of claim 1, wherein the simulation circuit is configured to generate the simulated medical breast image such that the breast is represented by a volumetric mesh including the surface mesh and a volume mesh.

6. The device of claim 5, wherein the correction circuit is configured to determine the corrections by applying a surface warping.

7. The device of claim 5, wherein the correction circuit is configured to determine the corrections by applying a displacement calculation for driving the surface mesh towards the surface scan image.

8. The device of claim 5, wherein the correction circuit is configured to determine the corrections by applying a Laplacian mesh smoothing for regularizing the volume mesh.

9. The device of claim 5, wherein the correction circuit is configured to apply an area constraint for reducing local changes in the surface area of the breast surface.

10. The device of claim 5, wherein the correction circuit is configured to apply a self-intersection prevention for avoiding mesh intersections.

11. The device of claim 1, wherein the medical breast image is a supine CT image, a prone MRI image, or a mammographic image.

12. The device of claim 1, wherein the scan image is an upright scan image and wherein the simulation circuit is configured to generate an upright simulated medical breast image.

13. An imaging system comprising:
   a medical image acquisition device that acquires a medical breast image of subject's breast potentially showing artificial deformations of the breast,
   a scan image acquisition device that acquires a scan image of the subject's breast showing the breast in a predetermined position of the subject and comprising surface information of the breast,
   a device as claimed in claim 1 that corrects the medical breast image acquired by the medical image acquisition device based on the acquired scan image, and
   an output device that displays the corrected medical breast image.

14. A method comprising:
obtaining a medical breast image of a subject's breast potentially showing artificial deformations of the breast,
obtaining a scan image of the subject's breast showing the breast in a predetermined position of the subject and comprising surface information of the breast,
generating a simulated medical breast image from the obtained medical breast image, the simulated medical breast image showing the breast in the same predetermined position of the subject as the scan image and representing the breast surface by a surface mesh,
  wherein the simulated medical breast image is generated based on a volumetric biomechanical model, and
  wherein material parameters of the biomechanical model are varied for aligning the biomechanical model with the breast surface extracted from the scan image,
determining corrections for correcting the simulated medical breast image for the artificial deformations based on the scan image by applying a surface matching between the surface mesh and the scan image,
applying the determined corrections to the obtained medical breast image to obtain a corrected medical breast image, and
displaying the corrected medical breast image.

15. A non-transitory computer-readable medium that includes a program that, when executed by a processing system, causes the processing system to:
obtain a medical breast image of a subject's breast potentially showing artificial deformations of the breast,
obtain a scan image of the subject's breast showing the breast in a predetermined position of the subject and comprising surface information of the breast,
generate a simulated medical breast image from the obtained medical breast image, the simulated medical breast image showing the breast in the same predetermined position of the subject as the scan image and representing the breast surface by a surface mesh,
  wherein the simulated medical breast image is generated based on a volumetric biomechanical model, and
  wherein material parameters of the biomechanical model are varied for aligning the biomechanical model with the breast surface extracted from the scan image,
determine corrections for correcting the simulated medical breast image for the artificial deformations based on the scan image by applying a surface matching between the surface mesh and the scan image,
apply the determined corrections to the obtained medical breast image to obtain a corrected medical breast image, and
display the corrected medical breast image.

16. The medium of claim 15, wherein the program causes the processing system to rigidly align the generated surface mesh to the breast surface extracted from the scan image to optimize the material parameters of the biomechanical model.

17. The medium of claim 15, wherein the program causes the processing system to determine a displacement vector field indicating the local corrections of the surface mesh, and to apply the displacement vector field to the obtained medical breast image to obtain the corrected medical breast image.

18. The medium of claim 15, wherein the program causes the processing system to determine the corrections by imposing a displacement constraint on skin nodes of the surface mesh such that the skin nodes coincide with the skin surface represented by the surface scan image.

19. The medium of claim 15, wherein the program causes the processing system to generate the simulated medical breast image such that the breast is represented by a volumetric mesh including the surface mesh and a volume mesh.

20. The medium of claim 15, wherein the program causes the processing system to determine the corrections by applying a displacement calculation for driving the surface mesh towards the surface scan image.

* * * * *